United States Patent
Rose et al.

(10) Patent No.: US 9,488,623 B2
(45) Date of Patent: Nov. 8, 2016

(54) GUIDED WAVE MODE SWEEP TECHNIQUE FOR OPTIMAL MODE AND FREQUENCY EXCITATION

(71) Applicant: The Penn State Research Foundation, University Park, PA (US)

(72) Inventors: Joseph L. Rose, State College, PA (US); Jason Philtron, Bellingham, WA (US)

(73) Assignee: The Penn State Research Foundation, University Park, PA (US)

( * ) Notice: Subject to any disclaimer, the term of this patent is extended or adjusted under 35 U.S.C. 154(b) by 221 days.

(21) Appl. No.: 14/506,151

(22) Filed: Oct. 3, 2014

(65) Prior Publication Data

US 2015/0135836 A1 May 21, 2015

Related U.S. Application Data

(60) Provisional application No. 61/886,397, filed on Oct. 3, 2013.

(51) Int. Cl.
*G01N 29/07* (2006.01)
*G01N 29/34* (2006.01)
*G01N 29/04* (2006.01)

(52) U.S. Cl.
CPC .............. *G01N 29/34* (2013.01); *G01N 29/04* (2013.01); *G01N 2291/011* (2013.01); *G01N 2291/106* (2013.01)

(58) Field of Classification Search
CPC ........... G01N 29/07; G01N 2291/011; G01N 2291/106; G01N 29/34
USPC ........................................................... 73/597
See application file for complete search history.

(56) References Cited

U.S. PATENT DOCUMENTS

| | | | |
|---|---|---|---|
| 5,734,588 A | 3/1998 | Rose et al. | |
| 5,932,806 A | 8/1999 | Rose et al. | |
| 7,997,139 B2 | 8/2011 | Owens et al. | |
| 8,286,490 B2 * | 10/2012 | Ruzzene | G01S 15/88 73/596 |
| 2005/0004457 A1 * | 1/2005 | Moilanen | A61B 8/0875 600/437 |
| 2005/0268720 A1 | 12/2005 | Quarry | |

(Continued)

FOREIGN PATENT DOCUMENTS

WO 2013027187 A2 2/2013

OTHER PUBLICATIONS

Hosten, B. et al., "Measurement of elastic constants in composite materials using air-coupled ultrasonic bulk waves", JASA, 1996, 99(4), 2116-2123.

(Continued)

*Primary Examiner* — J M Saint Surin
(74) *Attorney, Agent, or Firm* — Duane Morris LLP

(57) ABSTRACT

A method of inspecting a structure is disclosed. The method generally comprises selecting a search region of a dispersion curve of the structure corresponding to one or more inspection parameters. The search region comprises at least one guided wave mode activation point not located on the dispersion curve. The method further comprises activating, using an inspection system comprising at least one transducer, a plurality of activation points located within the search region of the dispersion curve and identifying an optimal activation point for the one or more inspection parameters. The optimal activation point comprises at least one of the plurality of activation points producing an optimal response for the one or more inspection parameters.

19 Claims, 16 Drawing Sheets

(56) References Cited

U.S. PATENT DOCUMENTS

| | | | | |
|---|---|---|---|---|
| 2009/0048789 | A1* | 2/2009 | Yu | G01N 29/069 702/39 |
| 2013/0327148 | A1* | 12/2013 | Yan | G01N 29/34 73/628 |
| 2013/0343424 | A1* | 12/2013 | Zombo | G01N 25/72 374/117 |
| 2015/0053009 | A1* | 2/2015 | Yan | G01N 29/07 73/598 |
| 2015/0073729 | A1* | 3/2015 | Borigo | G01N 29/2412 702/39 |

OTHER PUBLICATIONS

Gao, H. and J.L. Rose, "Goodness dispersion curves for ultrasonic guided wave based SHM: A sample problem in corrosion montioring", The Aeronautical Journal, 2010, 114(1151), 49-56.

Li, J. and J. Rose, "Implementing Guided Wave Mode Control by Use of a Phased Transducer Array", IEEE Transactions on Ultrasonics, Ferroelectrics, and Frequency Control, 2001, 48, 761-768.

Quarry, M. and J. Rose, "Multimode Guided Wave Inspection of Piping Using Comb Transducers", Materials Evaluation, 1999, 57, 1089-1090.

Zhu, W. and J. Rose, "Lamb Wave Generation and Reception with Time-Delay Periodic Linear Arrays: A BEM Simulation and Experimental Study", IEEE Transactions on Ultrasonics, Ferroelectrics and Frequency Control, 1999, 46, 654-664.

Hay, T. and J. Rose, "Guided Wave Testing Optimization" Materials Evaluation, 1999, 60, 1239-1244.

Yan, F. and J. Rose, "Time delay comb transducers for aircraft inspection", The Aeronautical Journal, 2009, 113, (1144), 417-427.

Bongo, C. et al., "A spacing compensation factor for the optimization of guided wave annular array transducers", JASA, 2013, 133(1), 127-135.

Wilcox, P.D., "Omni-Directional Guided Wave Transducer Arrays for the Rapid Inspection of Large Areas of Plate Structures," IEEE Trans. Ultrason., Ferroelect., Freq., 2003, 50(6), 699-709.

Wilcox, P.D. et al, "The excitation and detection of Lamb waves with planar coil electromagnetic acoustic transducers", IEEE Trans. Ultrason., Ferroelect., Freq. 2005, 52(12), 2370-2383.

Salas, K.I. and C.E.S. Cesnik, "Guided wave excitation by a CLoVER transducer for structural health monitoring: theory and experiments", Smart Materials and Structures, 2009, 18, 075005.

Salas, K.I. and C.E.S. Cesnik, "Guided wave structural health monitoring using CLoVER transducers in composite materials", Smart Materials and Structures, 2010, 19, 015014.

Glushkov, E.V. et al., "Selective Lamb mode excitation by piezoelectric coaxial ring actuators", Smart Materials and Structures, 2010, 19, 035018.

Michaels, J.E. et al., "Multi-mode and multi-frequency guided wave imaging via chirp excitations", Proceedings of SPIE, Health Monitoring of Structural and Biological Systems, 2011, 7984, T. Kundu (Ed.), SPIE, pp. 798401:1-798401:11.

Rose, J.L., "Ultrasonic Waves in Solid Media", 1999, Cambridge University Press, New York, NY., pp. 1-287.

Rose, J.L., "Guided wave testing of water-loaded structures", Materials Evaluation, 2003, 61(1), 23-24.

Bostron, J. et al., "Bond Integrity of a plate wave guide on a half space", AIP Conference Proceedings, 1430, 1323-1330 (2012).

Bostron, J. et al., "Ultrasonic Guided Wave Bondline Inspection of Coatings on Metal Using Leaky Rayleigh Waves", ASNT 22nd Annual Research Symposium and Spring Conference, Mar. 2013, pp. 74-77, American Society for Nondestructive Testing, Site: Memphis, TN.

* cited by examiner

GUIDED WAVE MODE SWEEP TECHNIQUE FOR OPTIMAL MODE AND FREQUENCY EXCITATION

CROSS-REFERENCE TO RELATED APPLICATIONS

This application claims the benefit of U.S. Provisional Patent Appl. No. 61/886,397, filed Oct. 3, 2013 and entitled "GUIDED WAVE MODE SWEEP TECHNIQUE FOR OPTIMAL MODE AND FREQUENCY EXCITATION," which is incorporated herein by reference in its entirety.

FIELD OF THE INVENTION

This disclosure is generally related to guided wave inspection of plate structures. More specifically, the present disclosure is directed to identifying optimal mode excitation points based on quantifiable wave characteristics.

BACKGROUND

Guided waves are elastic waves which propagate in a medium where the boundary conditions of the waveguide define the distinct modes which exist. This is in contrast with traditional bulk wave ultrasound, for which elastic waves propagate in a medium whose two mode types, longitudinal and shear, are not changed by changes in boundary condition. For guided waves, an infinite number of distinct wave modes exist. Each wave mode has a distinct wave structure (i.e., displacement, stress, etc., distributions through the waveguide's thickness) which varies with mode and frequency. Dispersion curves illustrate the relationship between phase (or group) velocity and frequency for a particular waveguide. Each structure and waveguide will have a distinct set of dispersion curves, which identify the modes that exist in that waveguide. The choice of guided wave mode and frequency is important when performing an inspection.

Historically, optimal guided wave mode and frequency selection has been mysterious. A rise in the understanding of guided wave mechanics and the ability to calculate mode solutions using modern computing power has illuminated the subject. However, there are still situations for which the best mode choice is unknown or the material properties are unknown and proper mode and frequency selection choice still remains a mystery.

Previous studies considered the use of phased arrays for mode control in both piping and plate structures. For example, a phased comb array has been used to excite different order axisymmetric modes in pipe. A simple ring piezoelectric element does not provide control over the relative excited amplitude of L(0,1) and L(0,2) modes. Manual adjustment of comb array spacers on pipe may be used to produce different sets of modes. Since different mode points have different characteristics (displacement wave structures), different modes should be sensitive to different defect types. Phased array transducers have been used in both isotropic and anisotropic plates. Individual elements may be phased to change the excited guided wave modes. Circular coil EMATs have been used in a phased array to excite guided wave plate modes. These transducers were used to excite the A0 and S0 modes for defect detection. Wedge-shaped guided wave SHM transducers (or CLoVER transducers) have been used. CLoVER sectors are activated to individually to perform an angular scan.

DETAILED DESCRIPTION OF THE INVENTION

Proper mode and frequency selection can increase inspection efficiency, detection capability, and decrease environmental or other factors that may cause false positives or mask the desired signal. In various embodiments, a system and method are disclosed for identifying improved and/or optimal mode activation points. A mode and frequency may be adjusted to optimize one or more parameters. The one or more parameters to be optimized may be selected based on requirements of an inspection, such as, for example, to identify a specific defect type, provide greater penetrating power, and/or any other suitable parameters.

Figure 1A:
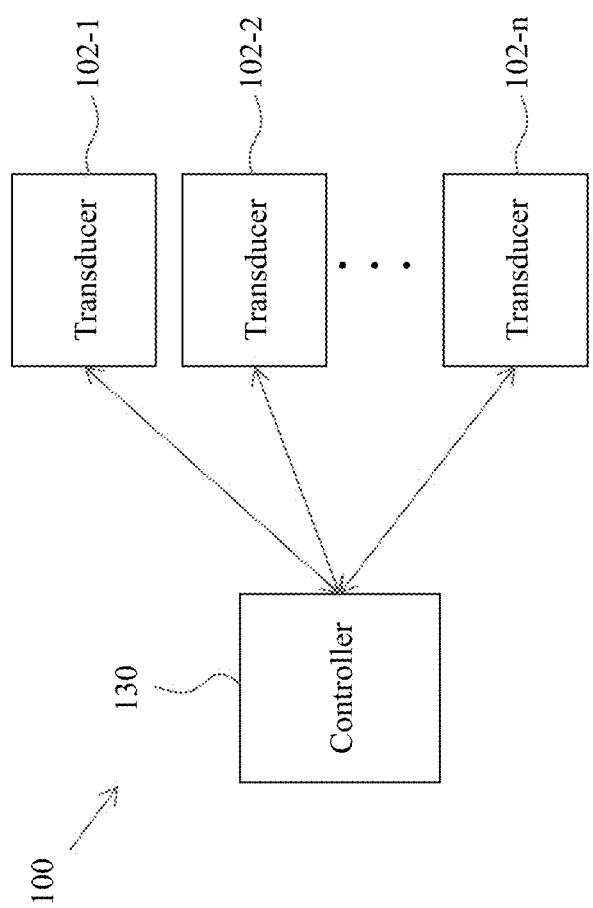
FIG. 1A illustrates one example of a non-destructive inspection system in accordance with some embodiments.
Figure 1B:
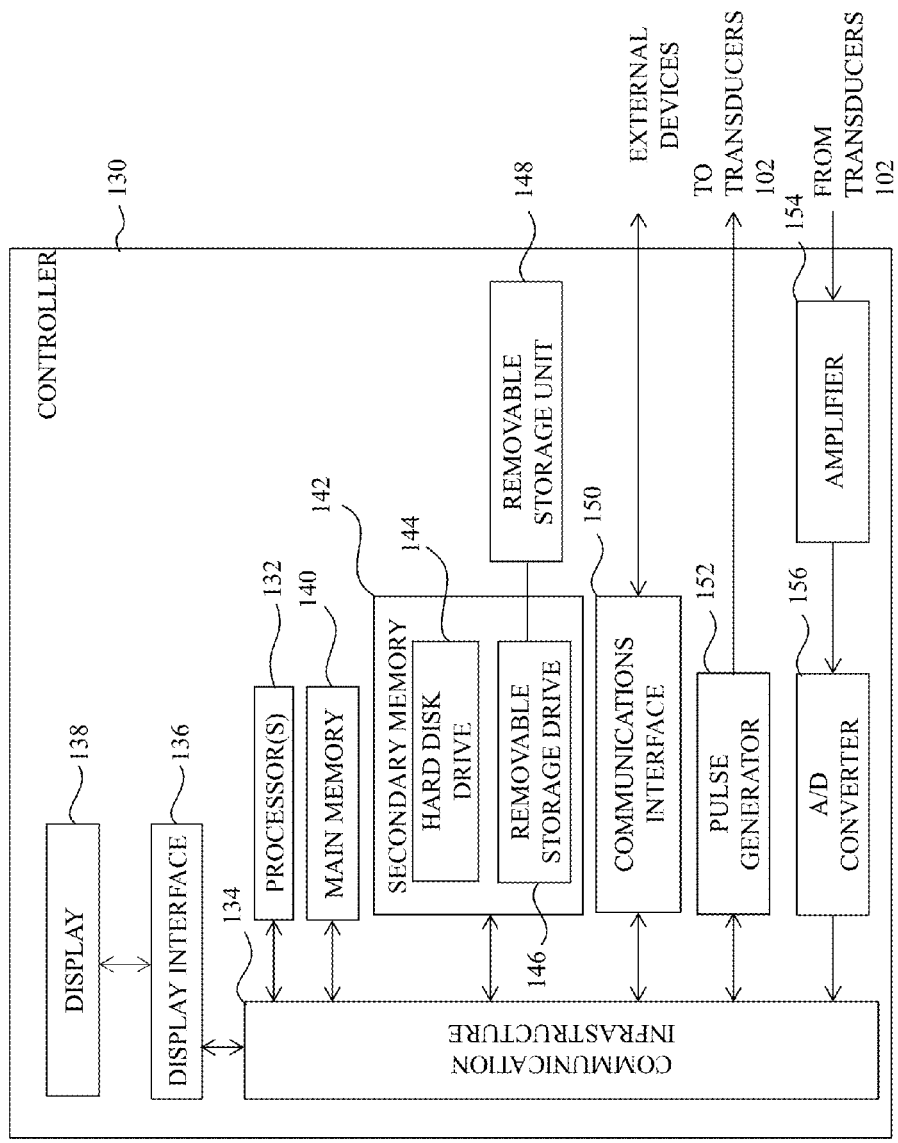
FIG. 1B illustrates one example of a block diagram of a controller of the non-destructive inspection system illustrated in FIG. 1A in accordance with some embodiments.

FIGS. 1A-1B illustrates one example of a non-destructive inspection system 100 configured to inspect plates and plate-like structures using guided wave arrays according to the embodiments disclosed herein. As shown in FIG. 1A, inspection system 100 includes a number, n, of transducers 102-1, 102-2, ..., 102-n (collectively "transducers 102") communicatively coupled to a controller 130. In some embodiments, system 100 is a "fixed" system in which the transducers are secured in some manner to a structure. These transducers 102 can be linear comb transducers, annular array transducers, arrays of individual single-element actuators, piezoelectric stack transducers, shear piezoelectric transducers, electromagnetic acoustic transducers ("EMATs"), magnetostrictive transducers, and/or other suitable transducers as will be understood by one of ordinary skill in the art. Transducers 102 can be configured as a transmitter or a receiver in a through-transmission setup. Each of the transducers 102 can also be used as a dual mode transducer under a pulse-echo test mode.

Referring now to FIG. 1B, controller 130 is disclosed. The controller 130 is configured to be coupled to the plurality of transducers 102. The controller 130 includes one or more processors, such as processor(s) 132. Processor(s) 132 may be any central processing unit ("CPU"), microprocessor, micro-controller, or computational device or circuit for executing instructions and be connected to a communication infrastructure 134 (e.g., a communications bus, cross-over bar, or network). Various software embodiments are described in terms of this exemplary controller 130. After reading this description, it will be apparent to one of ordinary skill in the art how to implement the method using other computer systems or architectures.

In some embodiments, controller 130 includes a display interface 136 that forwards graphics, text, and other data from the communication infrastructure 134 (or from a frame buffer not shown) for display on a monitor or display unit 138 that is integrated with or separate from controller 130.

Controller 130 also includes a main memory 140, such as a random access memory ("RAM"), and a secondary memory 142. In some embodiments, secondary memory 142 includes a persistent memory such as, for example, a hard disk drive 144 and/or removable storage drive 146, representing an optical disk drive such as, for example, a DVD drive, a Blu-ray disc drive, or the like. In some embodiments, removable storage drive may be an interface for reading data from and writing data to a removable storage unit 148. Removable storage drive 146 reads from and/or writes to a removable storage unit 148 in a manner that is understood by one of ordinary skill in the art. Removable storage unit 148 represents an optical disc, a removable memory chip (such as an erasable programmable read only memory ("EPROM"), Flash memory, or the like), or a programmable read only memory ("PROM")) and associated socket, which may be read by and written to by removable storage drive 146. As will be understood by one of ordinary skill in the art, the removable storage unit 148 may include a non-transient machine readable storage medium having stored therein computer software and/or data.

Controller 130 may also include one or more communication interface(s) 150, which allows software and data to be transferred between controller 130 and external devices such as, for example, transducers 102 and optionally to a mainframe, a server, or other device. Examples of the one or more communication interface(s) 150 may include, but are not limited to, a modem, a network interface (such as an Ethernet card or wireless card), a communications port, a Personal Computer Memory Card International Association ("PCMCIA") slot and card, one or more Personal Component Interconnect ("PCI") Express slot and cards, or any combination thereof. Software and data transferred via communications interface 150 are in the form of signals, which may be electronic, electromagnetic, optical, or other signals capable of being received by communications interface 150. These signals are provided to communications interface(s) 150 via a communications path or channel. The channel may be implemented using wire or cable, fiber optics, a telephone line, a cellular link, a radio frequency ("RF") link, or other communication channels.

In this document, the terms "computer program medium" and "non-transient machine readable medium" refer to media such as removable storage units 148 or a hard disk installed in hard disk drive 144. These computer program products provide software to controller 130. Computer programs (also referred to as "computer control logic") may be stored in main memory 140 and/or secondary memory 142. Computer programs may also be received via communications interface(s) 150. Such computer programs, when executed by a processor(s) 132, enable the controller 130 to perform the features of the method discussed herein.

In an embodiment where the method is implemented using software, the software may be stored in a computer program product and loaded into controller 130 using removable storage drive 146, hard drive 144, or communications interface(s) 150. The software, when executed by a processor(s) 132, causes the processor(s) 132 to perform the functions of the method described herein. In another embodiment, the method is implemented primarily in hardware using, for example, hardware components such as application specific integrated circuits ("ASICs"). Implementation of the hardware state machine so as to perform the functions described herein will be understood by persons skilled in the art. In yet another embodiment, the method is implemented using a combination of both hardware and software.

Controller 130 also includes a pulse generator 152 configured to output a variety of pulses to transducers 102. For example, pulse generator 152 may transmit time-delayed control signals to transducers 102 and/or pulse generator 152 may transmit control signals of varying amplitudes to transducers 102. In some embodiments, the pulse generator 130 is configured to alter the sensor phasing of the transducer 102 to activate one or more activation points within a dispersion curve space.

An amplifier 154 is configured to amplify signals received from transducers 102. Such signals received by transducers 102 include reflections of waves from structural features and other anomalies, e.g., corrosion in a plate or plate-like structures, in response to signals transmitted by pulse generator 152. An analog to digital ("A/D") converter 156 is coupled to an output of amplifier 154 and is configured to convert analog signals received from amplifier 154 to digital signals. The digital signals output from A/D converter 156 may be transmitted along communication infrastructure 134 where they may undergo further signal processing by processor(s) 132 as will be understood by one of ordinary skill in the art.

In some embodiments, guided wave mode choice may be a critical component in nondestructive evaluation and inspection and structural health monitoring by the nondestructive inspection system 100. In some applications, the material properties of a material to be inspected may not be well known (e.g., anisotropic composites) and/or other characteristics of the waveguide are not well characterized. One or more mode sweep methods may be used to experimentally and quantitatively assess available guided wave modes to optimize mode and frequency selection for inspection and/or monitoring of structures, such as, for example, plate like structures, plates, pipes, multilayer structures, curved plate structures, structures having a length to thickness ratio of 10 or more and/or any other suitable structures.

In one embodiment, the inspection system 100 comprises a plurality of multiple element transducers 102. The transducers 102 may be activated by the controller 130 with one or more time delays to activate one or more guide wave modes in localized and/or general regions of a dispersion curve for a plate-like structure. The controller 130 is configured to alter the sensor phasing to execute the transducers 102 at different activation points. For example, the controller 130 may be configured to introduce a time delay between two signals generated by the transducers 102 to activate one or more guided wave modes.

Figure 2:
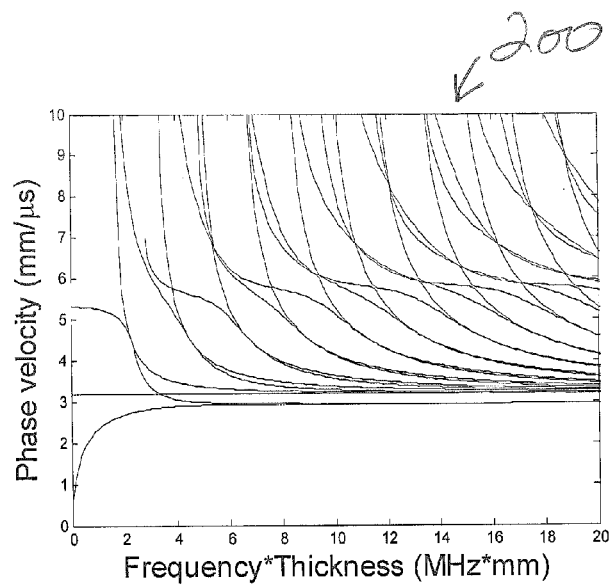
FIG. 2 is a graph depicting phase velocity dispersion curves for a steel plate in accordance with some embodiments.
Figure 3A:
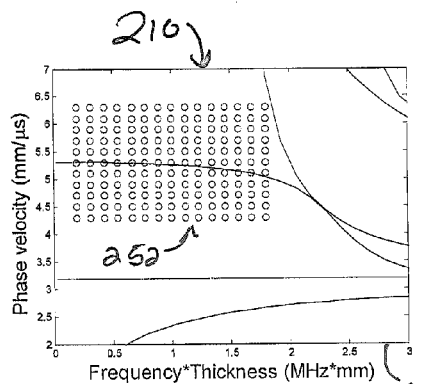
FIG. 3A is a graph depicting mode sweep regions in local scan mode in accordance with some embodiments.

In one embodiment, to perform a mode sweep of a structure, a sequence of points from a dispersion curve region are chosen. Each mode point is activated by the inspection system 100 in the structure, such as, for example, by introducing a time delay into the system 100. Received signals are analyzed, for example, by the controller 130, to determine an optimal mode point for one or more inspection parameters. For example, FIG. 2 illustrates a dispersion curve 200 for a steel plate. The controller 130 may perform a mode sweep in the steel plate to optimize one or more inspection parameters. In some embodiments, a local scan (or perturbation-type scan) is performed. The controller 130 selects a guided wave mode point from the dispersion curve 100 and performs a mode sweep in an area around the selected guide wave mode point. FIG. 3A illustrates one example of a local mode sweep 210 having a mode sweep focused near a single mode point (S0) and a selected frequency. Multiple guided wave mode solutions and the corresponding mode activation points 252 are excited by the inspection system 100 during a mode sweep. The horizontal axis 256 is shown as frequency times thickness due to the scaling of guided wave mode solutions with frequency as the thickness of the plate is changed.

Figure 3B:
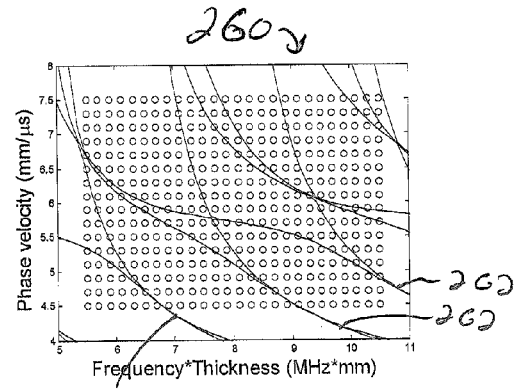
FIG. 3B is a graph depicting global scan mode in accordance with some embodiments.

In some embodiments, a global (or random) scan is performed by the inspection system 100 to identify an optimal mode and frequency for one or more inspection parameters. In a global scan mode, the controller 130 identifies a region of the dispersion curve 200 encompassing multiple modes and performs a mode sweep in the selected region (in contrast to a local sweep, which encompasses only a single mode point or mode crossing). The search region may comprise a small, moderate, or large sized section of the dispersion curve 200 that encompasses a plurality of modes. FIG. 3B illustrates one embodiment of a global scan 260 over a selected region. In the illustrated embodiment, the mode sweep 260 encompasses multiple modes 262a. The global scan may identify regions of interest of the dispersion curve 200 that encompass a single mode point or mode crossing. One or more local scans may be performed to optimize the one or more selected parameters within the regions of interest.

In various embodiments, a mode sweep may be performed with a single and/or multiple transducers 102. Multiple transducers 102 may be preferred to perform a global scan in less time, as compared to single element systems. The transducers 102 may comprise any suitable transducer, such as, for example a phased linear comb transducer, phased annular array, magnetostrictive, EMATS, laser actuation transducers, and/or any other suitable actuator type. In some embodiments, a phased array type may require adjustments to one or more phasing equations to account for the guided wave mode activation based on the actuator type and geometry. In some embodiments, the mode sweep resolution may be adjusted by the controller 130 based on one or more parameters of the scan. For example, for a quick scan, only a few activation points may be used while for detailed scans, many activation points may be used. Any suitable number of activation points may be selected based on one or more search and/or inspection parameters.

In various embodiments, the inspection system 100 may use any suitable form of guided wave mode excitation to perform a mode sweep, such as, for example, angle beam guided wave mode excitation and/or linear comb transducers. Excitation methods may produce unique excitation patterns. Although the transducer excitation patterns are discussed herein in terms of activation lines and points, complex excitation patterns may occur depending on the transducer type, dimensions, and other settings.

In various embodiments, the disclosed guided wave mode sweep techniques may be used to identify guided wave modes that exist in a structure having an unknown composition, may be used to specifically examine a transducer excitation spectrum (or a portion thereof) to determine which guided wave modes are able to be excited and/or may be used to provide one or more optimal parameters to the inspection system 100. In some embodiments, the inspection system 100 may be adjusted, for example, through guide wave mode sweep techniques, to identify one or more defect classes. Although specific defect classes are referred to herein, it will be recognized that the inspection system 100 can be optimized for any specific type, size, and/or location of a defect.

In various embodiments, the guided wave mode sweep techniques disclosed herein may be used in guided wave inspections, for example, in conjunction with pattern recognition algorithms for robust defect classification, with multiple modes for multiple state damage classification, and/or with any other suitable guided wave inspection solution. For example, in some embodiments, the controller 130 is configured to implement a guided wave mode sweep technique for use in materials of unknown and/or estimated properties, such as, for example, to identify material properties and/or defects in a plate, curved surface, pipe, and/or other geometry, where the material properties are unknown and/or for which only estimates are available, such as, for example, for anisotropic composite materials. In some embodiments, a maximum received wave amplitude can be used to map phase velocity dispersion curves, without moving the transducer or changing the transducer's couplant conditions. A global mode sweep can be performed for optimizing the transducer for the unknown material prior to inspection. Alternatively, dispersion curves may be generated from material property estimates. One or more local mode sweeps may be performed to optimize the transducer within the estimated optimal regions.

In some embodiments, the controller 130 may be configured to implement a mode sweep technique to activate multiple modes for robust defect detection and classification. For example, in some embodiments, multiple guided wave mode and frequency points may be activated and combined with pattern recognition algorithms to provide a greater increase in robustness by combining multiple features over multiple modes. Features from each activation point can be analyzed separately and combined by the controller 130 using pattern recognition, neural network, and/or other algorithms to combine the information into a robust defect classification scheme.

In some embodiments, the use of multiple modes may be beneficial when the defect sensitivity for different guided wave modes and/or frequency points is known. For example, in one embodiment, a first mode point may be used that is highly sensitive to damage initiation (e.g., crack initiation). Once damage is present (e.g., detected by the first mode point), a second mode point is activated to track the damage progression (e.g., crack growth). The second mode may be selected to optimize detection of damage progression while providing less sensitivity to additional damage initiation. Utilizing the mode sweep techniques disclosed herein, an inspection system 100 can be optimized for multiple damage states and/or levels of defect sensitivity.

In various embodiments, the controller 130 is configured to implement one or more guided wave mode sweeps to optimize one or more parameters to solve a specific inspection problem. For example, in some embodiments, the controller 130 is configured to implement one of a global scan mode and/or a local scan mode. If information is available indicating activation mode and frequencies, such as, for example, an estimated dispersion curve, a local scan mode may be executed to optimize the inspection system 100 within the identified regions of the dispersion curves. If no estimates are available for the feature and/or parameter to be optimized, a global mode scan is performed to identify regions of interest. After the global mode scan, one or more local scans can be performed to optimize the inspection system 100 within the identified regions of interest.

After optimizing the inspection system 100, the controller 130 activates the transducers 102 at the identified mode activation points. Waveforms received from each mode activation point are analyzed for one or more features changes and/or feature correlations to detect defect formation, severity, sizing, location, and/or any other desired inspection information. In some embodiments, one or more pattern recognition algorithms may be used to combine the information from single and/or multiple mode and frequency activation points and single and/or multiple features to create a robust defect classification algorithm. The selected activation points, features, and/or classification algorithms may be used to assess damage in additional structures.

In some embodiments, one or more mode sweep techniques, such as, for example, a global mode sweep technique and/or a local mode sweep technique, may be implemented with an emphasis on non-linear mode solutions which are sensitive to changes in microstructure materials. For non-linear mode solutions, specific mode phase velocity and frequency values may be utilized. Using a mode sweep technique, the non-linear guided wave solution may be optimized to generate non-linear harmonics, which can detect and magnify guided wave non-linearities in systems where non-linearities are present. Non-linear mode solutions may be used in global scan modes, local scan modes, and/or any other suitable guided wave scan mode.

Figure 4A:
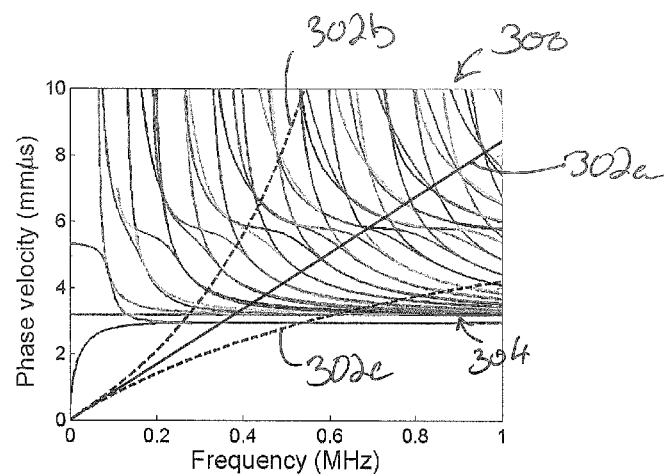
FIG. 4A depicts activation lines for a linear, multi-element, phased array comb transducer with in phase and linear time delay element excitation in accordance with some embodiments.

In some embodiments, one or more transducers 102 of the inspection system 100 comprise linear comb array transducers. A linear comb array transducer excites waves at a constant wavelength, given by a comb element spacing s. FIG. 4A illustrates phase activation lines 302a-302c for a linear comb array transducer overlaid on a dispersion curve 304 for one embodiment of a steel plate. The activation line 302a is an in-phase activation line and is generated by the linear comb array transducer when the elements of the transducer are activated in-phase. The activation line 302 starts at point (0,0) on the graph 300 and extends outward at an angle φ determined by the linear comb array transducer element spacing, wherein:

$$\phi = \tan(s) = \tan(\lambda_s) = \tan(c_p/f), \quad (1)$$

where φ is the angle of the activation line in $c_p$-f space from the positive horizontal axis, s is the element spacing, and λs is the wavelength of waves excited by the comb, which is equal to s.

Time delayed activation lines 302b, 302c are illustrated in FIG. 4A. When the elements of a linear comb array transducer are excited out of phase, such as, for example, with a linear time delay to successive elements (e.g., 0, 1τ, 2τ, 3τ, ... ), the activation line 302b, 302c curves. The upward curved activation line 302b illustrates the forward traveling wave activation line for a 1 μs time delay and the downward curved activation line 302c illustrates the backward traveling wave activation line for the 1 μs time delay. In some embodiments, the controller 130 is configured to implement one or more time delays to conduct a mode sweep through a region of the dispersion curve in $c_p$-f space with a single transducer applying different time delays (and frequencies), without the need to change the physical location, configuration, or condition of the single transducer. In other embodiments, a plurality of transducers 102 are activated by one or more time delays to sweep through a region of the dispersion curve 304. In some embodiments, the element spacing "s" may comprise any suitable spacing such as, for example, 8.43 mm. The illustrated mode sweep 302a-302c utilizes a 1 μs time delay (τ). Although a 1 μs time delay is illustrated, any suitable time delay may be implemented to alter the activation frequency and activate specific regions of the dispersion curve 304.

In some embodiments, the controller 130 may be configured to derive a suitable time delay and/or phase velocity for a selected mode sweep. In one embodiment, the wavelength that will be excited in a transducer, such as a linear phase comb transducer, is:

$$\lambda = \lambda_s \pm \lambda_{change\text{-}TD}, \quad (2)$$

where $\lambda_s$ is the wavelength excited based on the physical dimension of the transducer ($\lambda_s = c_p/f = s$), and $\lambda_{change\text{-}TD}$ is the change in the wavelength excited due to the linear time delay, τ, applied to the individual elements of the transducer ($\lambda_{change\text{-}TD} = c_p\tau$). Substituting into equation 2:

$$\lambda = c_p/f \pm c_p\tau. \quad (3)$$

Equation 3 may be rearranged to solve for a selected phase velocity (cp):

$$\lambda = c_p(1/f \pm \tau^* f/f), \quad (4)$$

$$c_p = f_s/(1 \pm \tau f) \quad (5)$$

Equation 3 may be further rearranged to solve for a linear time delay:

$$\pm c_p\tau = s - c_p/f, \quad (6)$$

$$\tau = 1/f \pm s/c_p. \quad (7)$$

In Equations (2) through (7), "+" indicates forward-traveling waves and "−" indicates backward traveling waves. The forward-traveling wave activation line has an effectively larger wavelength (or spacing) then the backward-traveling wave activation line.

Figure 5A:
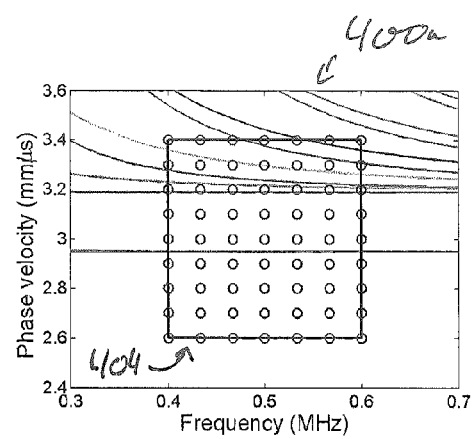
FIG. 5A depicts a phased array mode sweep activation points in $c_p$-f space.

The effective wavelength is different from the comb spacing, "s" due to the application of the linear time delay τ. This delay, to the ith element, is (i−1)τ. The controller 130 may be configured to select various time delays (TD) and frequencies (f) to perform a systematic sweep over an area of mode activation points in $c_p$-f space. For example, as shown in FIG. 5A, in one embodiment, an activation region 404 of a dispersion curve 300 may be selected for excitation. In the illustrated embodiment, the region of the dispersion curve is selected near a guided wave mode at 0.5 MHz and 2.95 mm/μs.

Figure 5B:
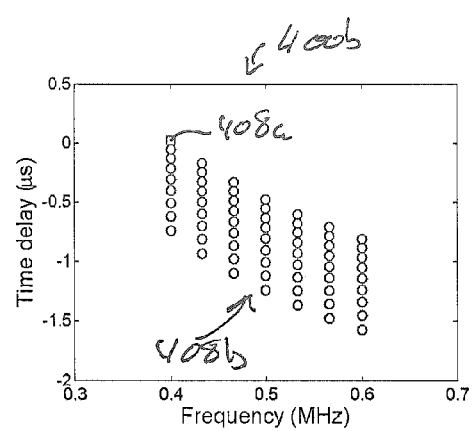
FIG. 5B depicts a phased array mode sweep activation points in TD-f space.

In various embodiments, the time delay needed to activate one or more specific mode points will depend on frequency, according to Equation (5) above. Because the time delay is frequency specific, the rectangular activation grid 404 illustrated in FIG. 5A is distorted when illustrated in a time delay plot as shown in FIG. 5B. The further the mode activation point is from the phase activation line, the greater the time delay needed to sweep the mode activation point.

In the example illustrated in FIG. 5B, a single mode point 408a is located above a selected phase activation line, with the remainder of the mode points 408b being located below the phase activation line. To activate the single mode point 408a located above the phase activation line, a positive time delay is introduced by the controller 130. To activate the mode points 408b located below the phase activation line, a negative time delay is required.

A negative time delay is equivalent to a backwards traveling wave. In some embodiments, the inspection system 100 is configured to introduce a negative time delay, such as, for example, through hardware or software. In some embodiments, the inspection system 100 generates an equivalent to a negative time delay by reversing the order of connecting wires and/or rotating a transducer 180 degrees such that the backwards traveling waves are transmitted in the direction of a receiver. Table 1 illustrates one embodiment of a plurality of time delays configured to activate each of the mode activation points illustrated in FIGS. 4A and 4B.

TABLE 1

| $c_p \backslash f$ | 400 | 433 | 467 | 500 | 533 | 567 | 600 |
|---|---|---|---|---|---|---|---|
| 2.6 | −0.742 | −0.935 | −1.100 | −1.242 | −1.367 | −1.478 | −1.576 |
| 2.7 | −0.622 | −0.815 | −0.979 | −1.122 | −1.247 | −1.358 | −1.456 |
| 2.8 | −0.511 | −0.703 | −0.868 | −1.011 | −1.136 | −1.246 | −1.344 |
| 2.9 | −0.407 | −0.599 | −0.764 | −0.907 | −1.032 | −1.142 | −1.240 |
| 3.0 | −0.310 | −0.502 | −0.667 | −0.810 | −0.935 | −1.045 | −1.143 |
| 3.1 | −0.219 | −0.412 | −0.577 | −0.719 | −0.844 | −0.955 | −1.053 |
| 3.2 | −0.134 | −0.327 | −0.492 | −0.634 | −0.759 | −0.870 | −0.968 |
| 3.3 | −0.055 | −0.247 | −0.412 | −0.555 | −0.680 | −0.790 | −0.888 |
| 3.4 | 0.021 | −0.172 | −0.337 | −0.479 | −0.604 | −0.715 | −0.813 |

Figure 4B:
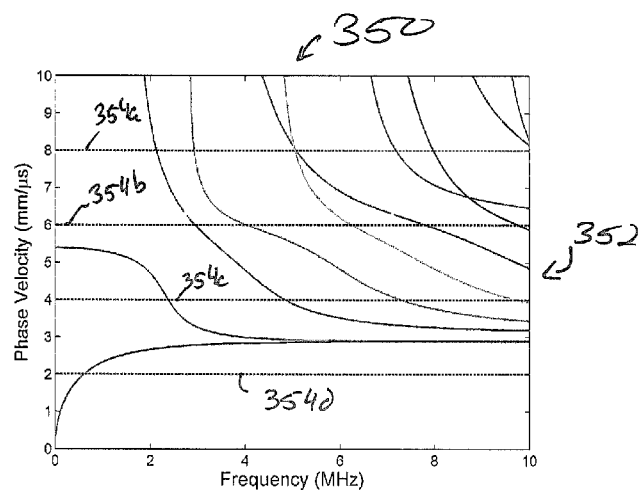
FIG. 4B depicts activation lines for an angle beam probe.

FIG. 4B is graph 350 illustrating one embodiment of a dispersion curve 352 showing horizontal activation lines 354a-354d generated by an angle beam probe. Each activation line 354a-354d corresponds to a different scan angle of the angle beam probe. The scan angle is adjusted to sweep through a region of the dispersion curve 352 to perform a local and/or a global scan identifying one or more optimal guided wave mode activation points.

In various embodiments, the disclosed systems and methods are directed to fine tuning of a guided wave inspection system within a region of a dispersion curve. Fine tuning within the region involves activating guided wave modes within a fine grid. The fine grid is utilized to optimize a choice of mode end frequency for solving a particular inspection problem. In contrast, a coarse grid is related to a scan over the phase velocity-frequency space to provide a reasonable estimate of the phase velocity dispersion curve, the result of which would be somewhat close to the theoretical calculation of the curves based on material property and thickness estimates. Although coarse grids can provide the wave guide structure of a plate, plate-like, or pipe structure being studied, the given material and geometrical properties of a structure are often incorrect (or unknown) and the generated dispersion curve from the coarse grid may be inaccurate. The fine tuning grid compensates for this error by finding the precise location and phase velocity dispersion curve space in creating an effective "wave resonance." The identified guided wave mode activation points magnify the amplitude, often significantly, of a specific feature-type, providing a guided wave structure value that is optimally sensitive to a particular inspection problem. The method may be particularly useful for solving subtle defect inspection problems. For example, in some embodiments, a coarse grid frequency spacing may comprise a spacing of over 100 KHz and a fine grid frequency spacing may comprise a spacing of less than 10 KHz. Phase velocity values may also be at a difference factor of 10 or greater in some embodiments.

Features of interest include, for example, in-plane displacement or out of plane displacement for example on the outer surface or the center of a structure, at an interface along a bonding layer, or shear stress at an interface. Many other features are related to wave structure and location across the thickness and can be used to optimize the guided wave mode inspection system, and are within the scope of this disclosure.

The guided wave inspection system 100 may be configured to perform a coarse search (utilizing a coarse grid) to provide a rough estimate of the dispersion curve for a structure. The guided wave inspection system 100 is then configured for a fine tuning grid (or fine search) to identify precise points in the phase velocity dispersion curve space for inspection success and optimization. The disclosed systems and methods are configured to use fine tuning for enhancement to solve a problem at all is now made possible because of the improvement in sensitivity as a result of the fine tuning methods disclosed herein.

Theoretical calculations of the phase velocity dispersion curves are based on reasonable estimates of material and geometrical properties and ideal experimental condition of plane infinite continuous waves. However, experimental generation of the dispersion curves includes the influence of the instrumentation and transducer parameters used in the specific experiment, which leads to including the source influence of the transducer being used.

Figure 6A:
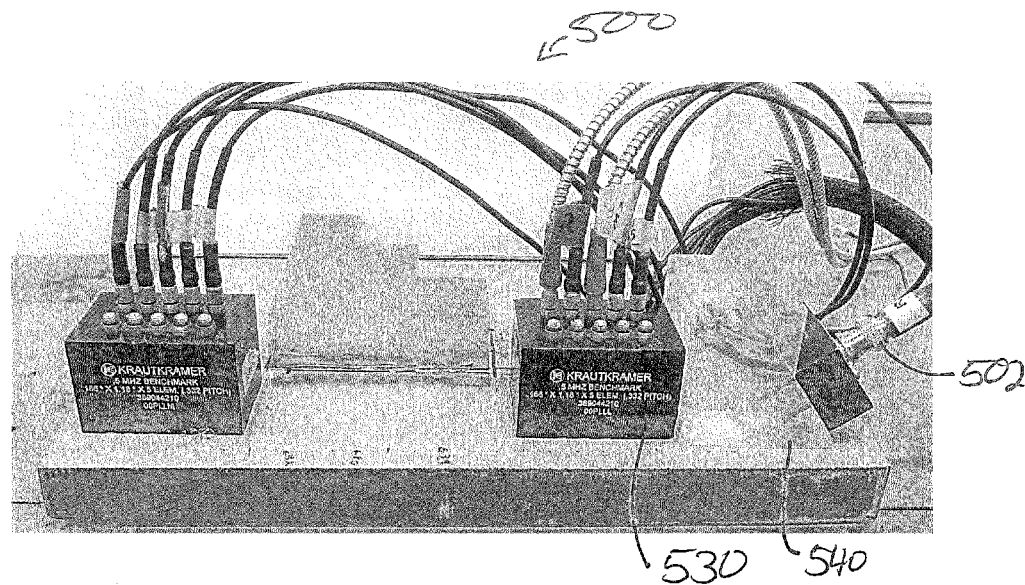
FIG. 6A depicts a measurement setup for through-transmission mode using a phased array comb transducer for mode activation.

FIG. 6A illustrates one embodiment of an inspection system 500 configured to perform a mode sweep method as disclosed herein. The inspection system 500 is similar to the inspection system 100 described in conjunction with FIGS. 1A-1B. The inspection system 500 comprises a linear comb transducer 502 and a controller 530. The transducer 502 is configured to generate one or more guided waves in a plate-like structure 540. In one embodiment, data was collected at specific mode activation points to perform a mode sweep similar to the one shown in FIGS. 5A-5B. In one embodiment, a scan region (region of interest) is focused around a single guided wave mode and frequency point which is an educated guess about what mode points may be useful for inspection, e.g., the inspection system 500 may be configured to perform a local scan within a region of a dispersion curve for the plate-like structure 540. The inspection system 500 was used to perform experimental confirmation of the methods disclosed herein.

Figure 6B:
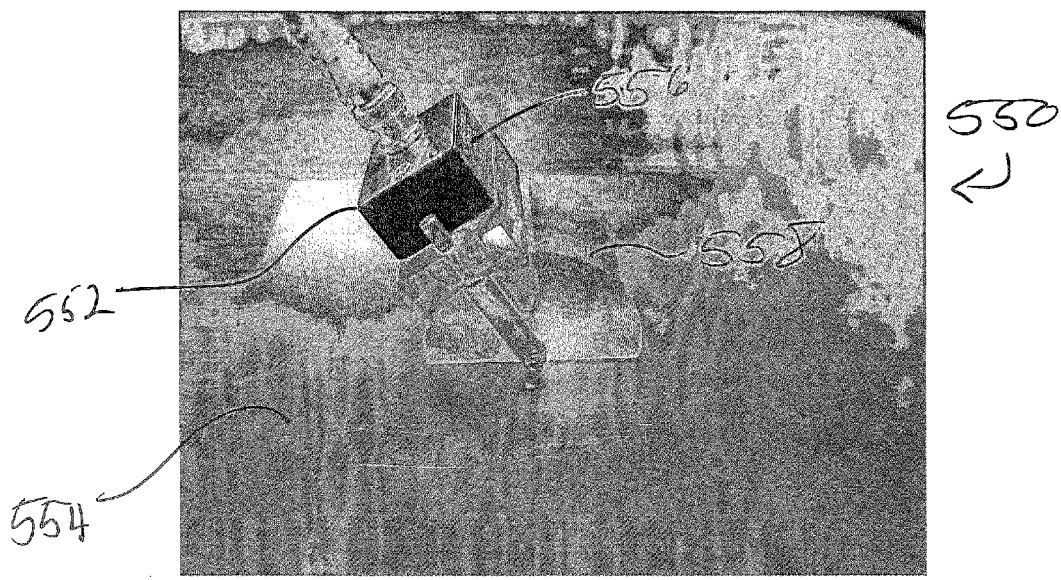
FIG. 6B depicts a measurement setup for through-transmission mode using an angle beam probe for mode activation.

FIG. 6B illustrates one embodiment of an inspection system 550 configured to perform a guide wave mode sweep method as described herein. The inspection system 550 comprises an angle beam probe 552 coupled to a plate-like structure 554. The angle beam probe 552 comprises a transducer 556 coupled to a wedge 558 such that the angle of the transducer 556 relative to the plate-like structure 554 may be adjusted. The angle beam probe 552 is placed on the surface of the plate-like structure 554 and is activated to generate guide waves within the plate-like structure 554. The angle of the angle beam probe 552 is adjusted to excite varying phase velocity values (e.g., guide wave modes) when performing a scan within a region of the dispersion curve of the plate-like structure 554. The inspection system 550 was used to perform experimental confirmation of the methods disclosed herein.

Each received waveform may be analyzed using signal processing to determine the value of each feature of interest. These feature values are assessed to determine which mode points are optimal for the given application. We discuss optimization for three characteristics: penetration power, defect sensitivity using the energy ratio feature, and defect sensitivity using the frequency shift feature. Note that optimization may be performed for a variety of features, including, but not limited to: amplitude, amplitude ratio, arrival time, energy, energy ratio, signal difference coefficient (SDC), max frequency, frequency shift, frequency ratio, wave packet kurtosis, wave packet skewness, etc.

The data and analysis shown in this section was performed on a 1" steel plate with a 1" polymer coating bonded to it using epoxy. A side view of the sample is shown in FIG. 6A. The object of this nondestructive evaluation was to determine the optimal mode point(s) for bond evaluation. Note that in general any application can be addressed using the guided wave mode sweep methods described herein, and that the bond evaluation application is simply one of many applications.

In various embodiments, an inspection system 100 may be configured to perform a mode sweep to optimize one or more parameters, such as, for example, penetration power of the guided waves, an energy ratio feature of the guided waves, a frequency shift feature, and/or any other suitable parameter. In some embodiments, one or more parameters may be optimized based on requirements of an inspection. For example, in one embodiment, the time required to inspect large areas of materials may be reduced by optimizing the penetrating power of the guided waves.

The maximal inspection distance is dependent on a variety of factors. For example, in some embodiments, different transducer types cause different wave amplitudes in the inspected sample. The inspection frequency may affect transducer output as transducers have a limited frequency bandwidth. As another example, certain modes have greater attenuation than other modes. Modes with lower attenuation may allow a longer inspection distance.

Figure 7:
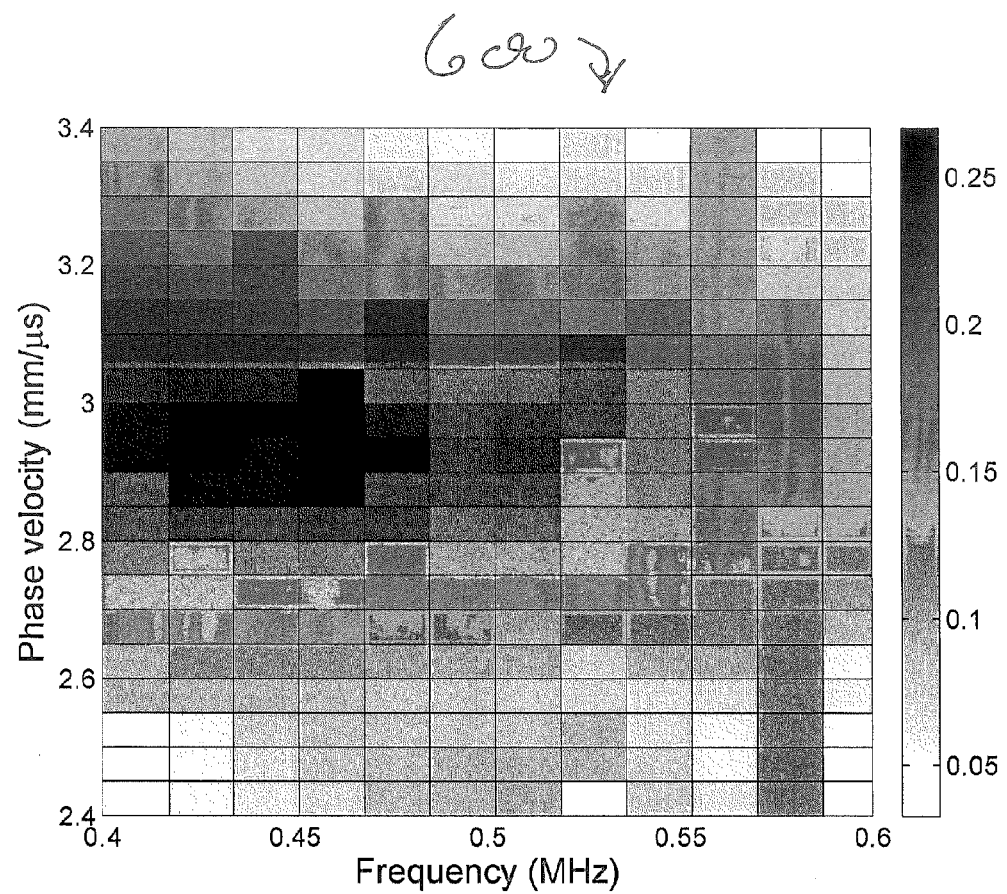
FIG. 7 depicts a plot of maximum wave amplitude for a Rayleigh wave on a bare steel surface.

In one embodiment, to maximize inspection distance, factors of frequency and mode selection are combined to show which modes create a signal with the highest amplitude, and thus the greatest inspection distance. The controller 130 activates a variety of guided wave mode points to determine the guided wave mode points having the highest signal amplitude. FIG. 7 illustrates a shaded scale plot 600 of one maximization determination for a plate like-structure, such as, for example, an HY-Steel surface. The plots are generated on a shaded scale in $c_p$-f space. FIG. 7 illustrates the signal amplitude of a guide wave traveling along the surface of the plate-like structure (e.g., the zero bond length case). The units of the scale plot 600 is volts. The guided wave mode points with the highest signal amplitude can be considered optimal for penetration power when inspecting with a Rayleigh wave on the plate-like structure. For example, in the illustrated embodiment, the optimal guided wave mode points occur near 2.95 mm/µs and at about 0.45 MHz, corresponding to the Rayleigh wave speed calculated for HY-100 Steel. The optimal mode point gives an increase in amplitude from the initial inspection starting point. For example, in the illustrated embodiment, a 8% increase in amplitude is provided by the optimal guided wave mode point.

In some embodiments, the frequency of a transducer, such as transducer 102, may be adjusted to identify an optimal guided wave mode point. For example, as shown in FIG. 7, the optimal transducer frequency for the inspection system 500 is about 0.45 MHz, which is less than the transducer 502 design frequency of 0.5 MHz. The optimal transducer frequency may be reduced by one or more factors, such as, for example, a damping material included in the transducer construction to increase bandwidth. Analyzing the activated mode points, the controller 130 determines that the optimal mode point for wave penetration.

Figure 8A:
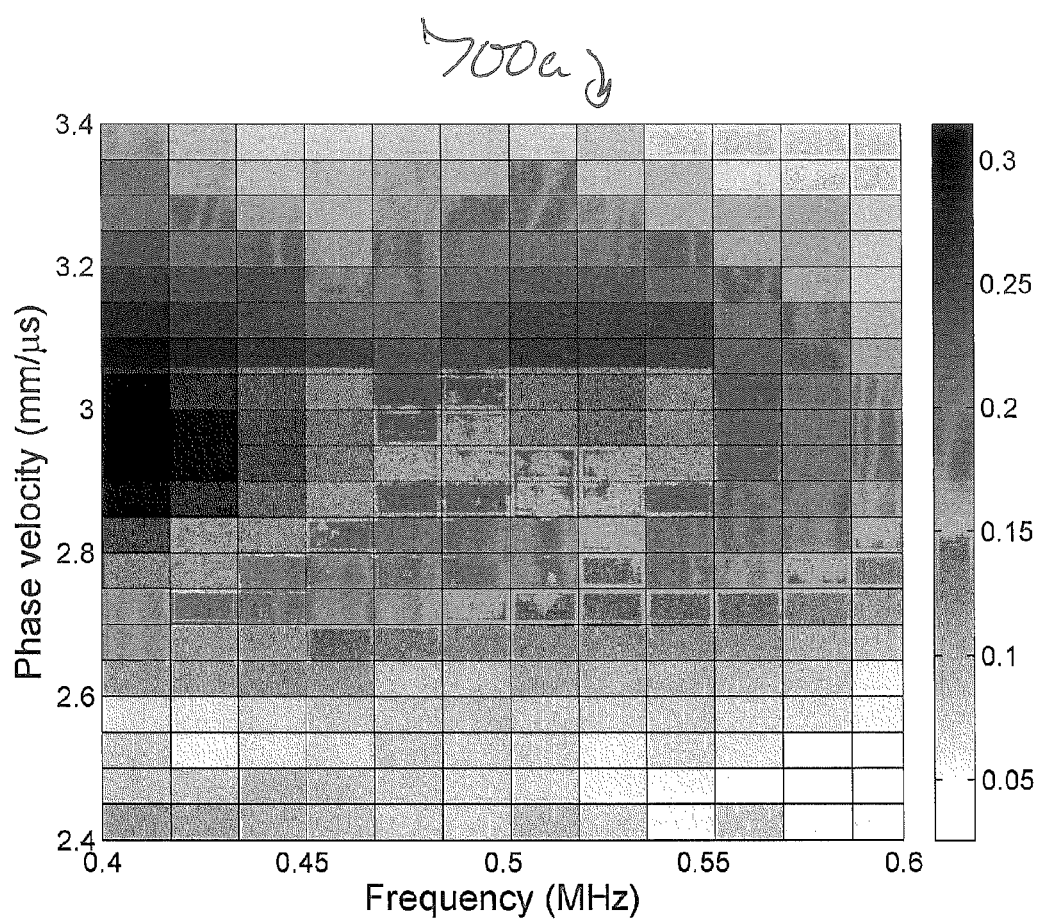
FIGS. 8A-8D depict a plot of maximum wave amplitude for the interface wave traveling in multiple defect classes.
Figure 8B:
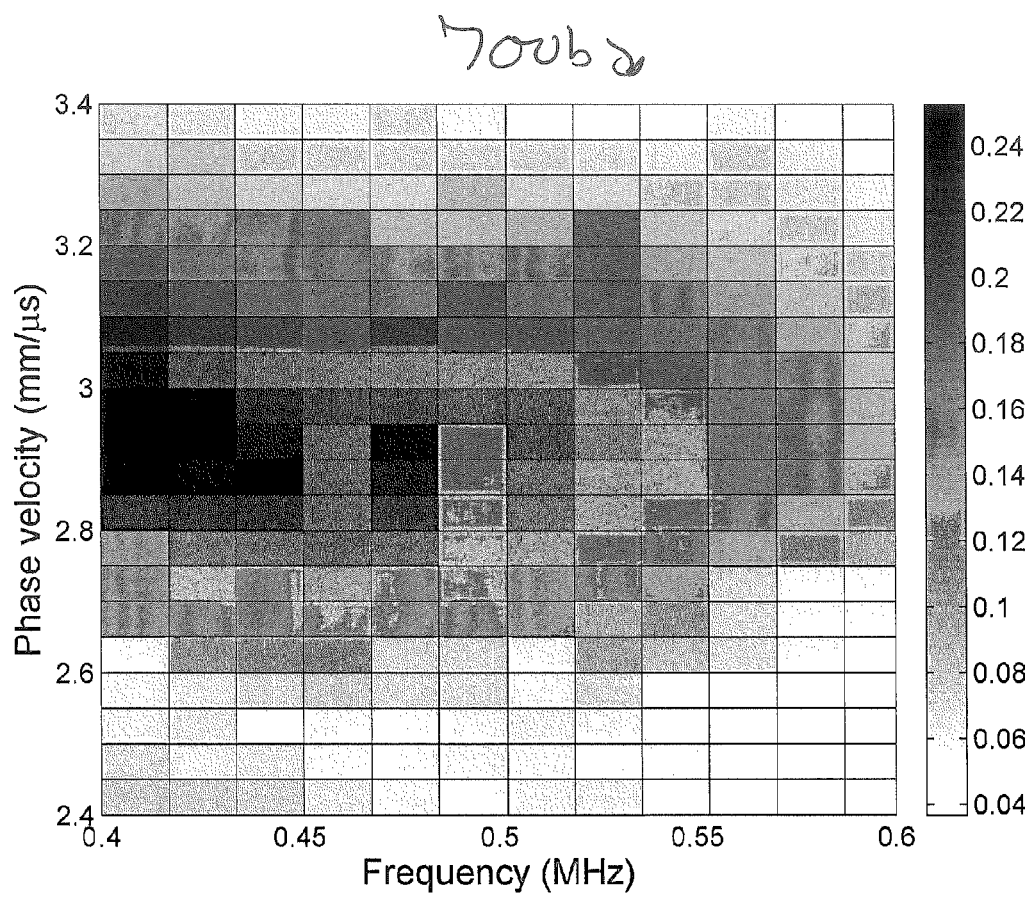
Figure 8C:
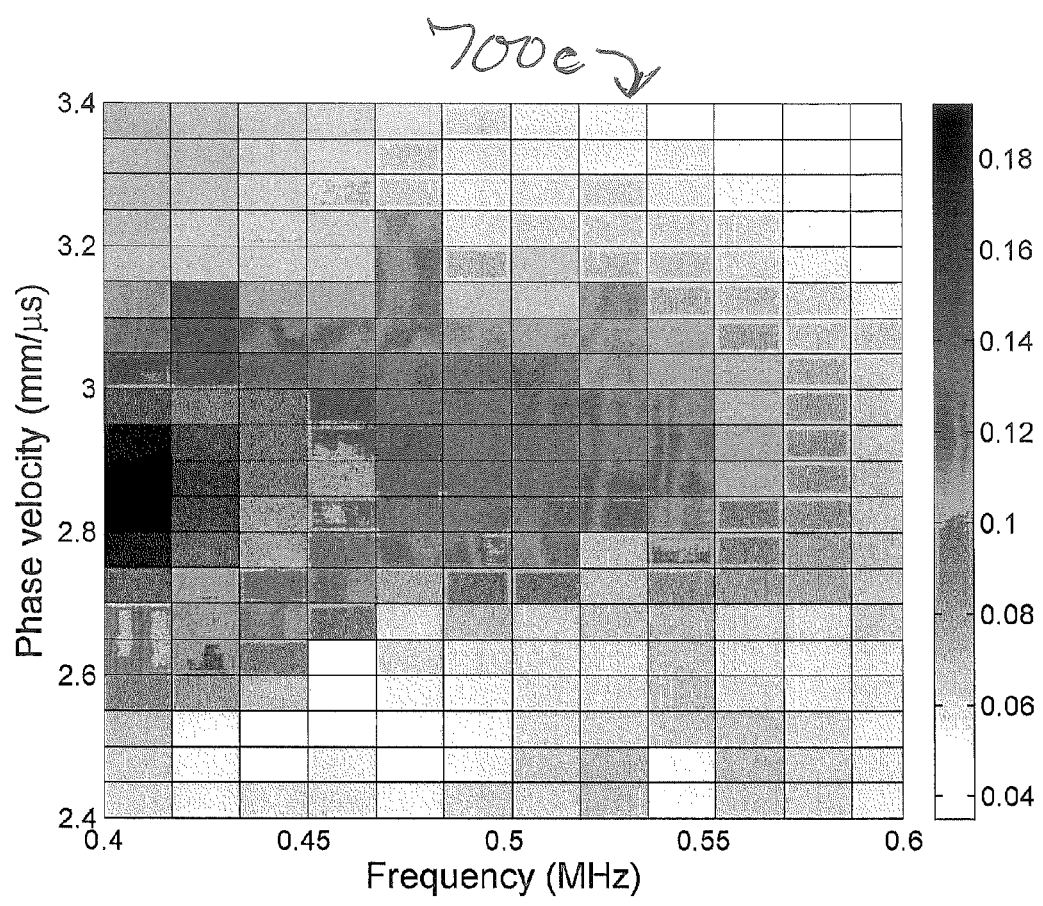

FIGS. 8A-8C are graphs 700a-700c illustrating signal amplitudes for guided waves traveling along an interface for bond lengths of 2.8, 5.9, and 9.0 cm respectively. The bond lengths are referred to herein as defect classes 1, 2, and 3. As shown in FIGS. 8A-8C, the mode point having the maximum amplitude tends to decrease in frequency as the defect class increases. The phase velocity remains relatively similar to the zero bond case (e.g., no defect case) for all defect classes. For defect class 3, the maximum amplitude is located at the edge of the selected sweep region 700c, or 0.4 MHz. It will be appreciated that the indicated amplitudes in FIGS. 8A-8C decrease with increased bond length, indicating that the maximum amplitude is lower for shorter defect conditions.

Figure 8D:
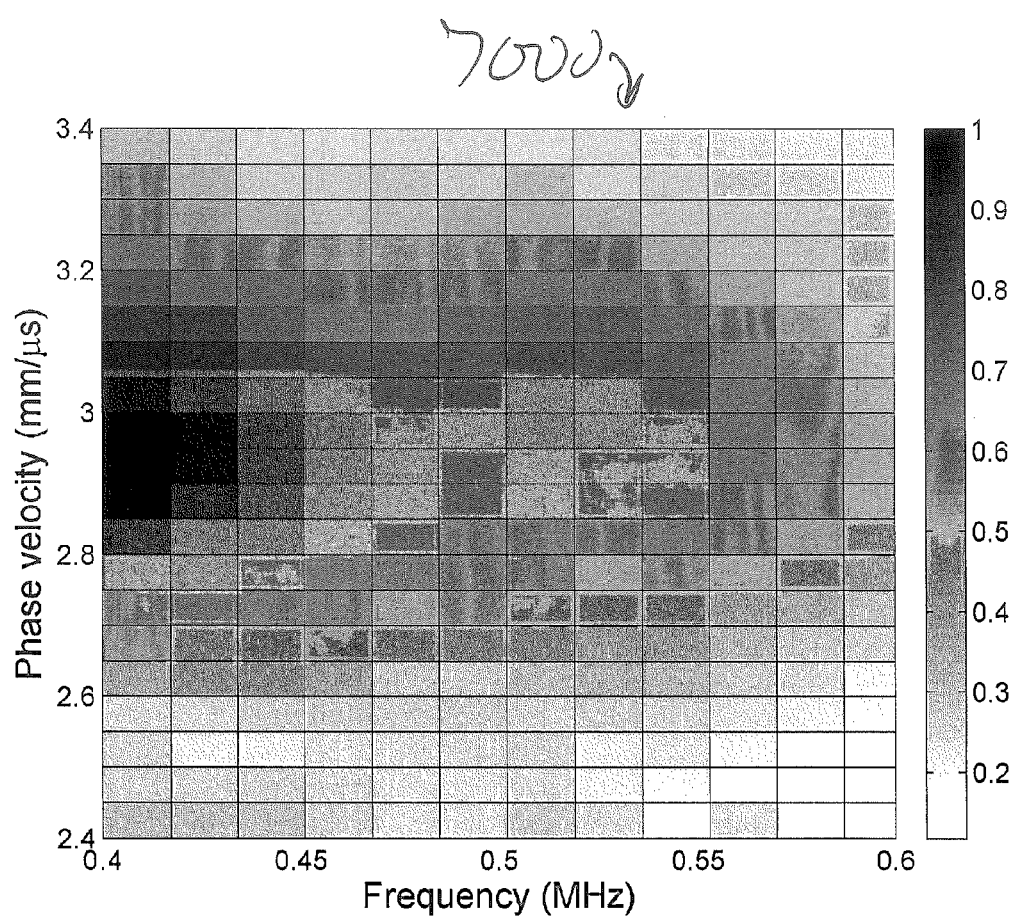

As shown in FIGS. 8A-8C, guided wave attenuation is frequency-dependent such that the optimum frequency for a maximum inspection distance depends on a variety factors, such as, for example, a transducer output, a desired inspection range, and/or a length of a defect (or disbond). For example, for inspections in which the guide waves travel a short distance, such as, for example, a couple of centimeters, a higher frequency mode may be used and the received wave signal may have a high signal to noise ratio. For inspections in which the guided waves travel a longer distance, such as, for example, distances covering tens of centimeters or more, a lower frequency mode is optimal, as the guided wave attenuation becomes the dominant factor over longer distances. FIG. 8D illustrates the mean of the received amplitudes 700d of the three defect classes, normalized by bond length. The optimal mode points are illustrated for the transducer 502 for bond inspection of defects similar to defect classes 1, 2, and 3. The identified optimal mode point has a 20% increase in amplitude from a calculated starting point.

In some embodiments, the controller 130 may be configured to use the optimal frequency determination as a search point for subsequent tuning of the inspection system 100. For example, in the embodiment illustrated in FIG. 8C, the identified optimal frequency of 0.4 MHz is located at the edge of the selected sweep region 700c, suggesting that optimal frequency for long distance inspection (e.g., penetration) may be located in a sweep region lower than the selected sweep region. In some embodiments, the controller 530 may execute additional mode sweeps using the identified optimal frequency as a starting point, for example, searching a selected sweep region of less than 0.4 MHz.

Figure 9:
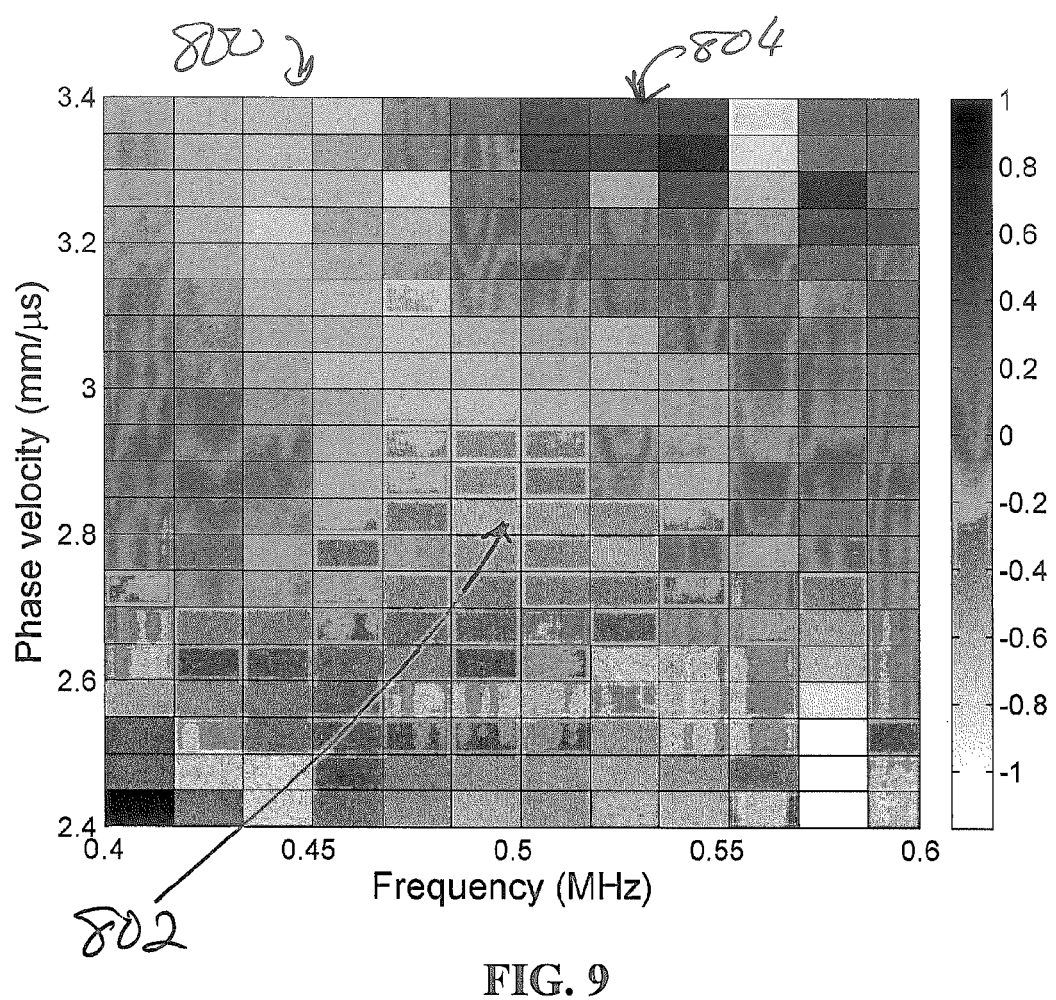
FIG. 9 depicts a plot of the mean of the energy ratio feature normalized by bond length for the illustrated defect classes.

In various embodiments, an inspection system 100 may be optimized based on an energy ratio parameter. The energy ratio parameter is calculated by summing the area under an amplitude envelope of a wave packet that travels through a bonded (or defect) region and normalizing by the wave that traveled in a non-bonded (or defect free) region. FIG. 9 is a graph 800 illustrating the mean of the energy ratio feature for the three defect classes discussed above with respect to FIGS. 8A-8C. In the embodiment illustrated in FIG. 9, the optimal mode activation region 802, e.g., the region having good feature sensitivity in the center of graph, is located at a phase velocity ($c_p$) of about 2.8 mm/µs and a frequency (f) of about 0.5 MHz. In the optimal mode activation region 802, the energy ratio feature value changes at a rate between −0.5 and 1 dB/cm. The optimal mode point in the optimal mode activation region gives a 106% increase in feature value from the selected starting point.

Figure 10:
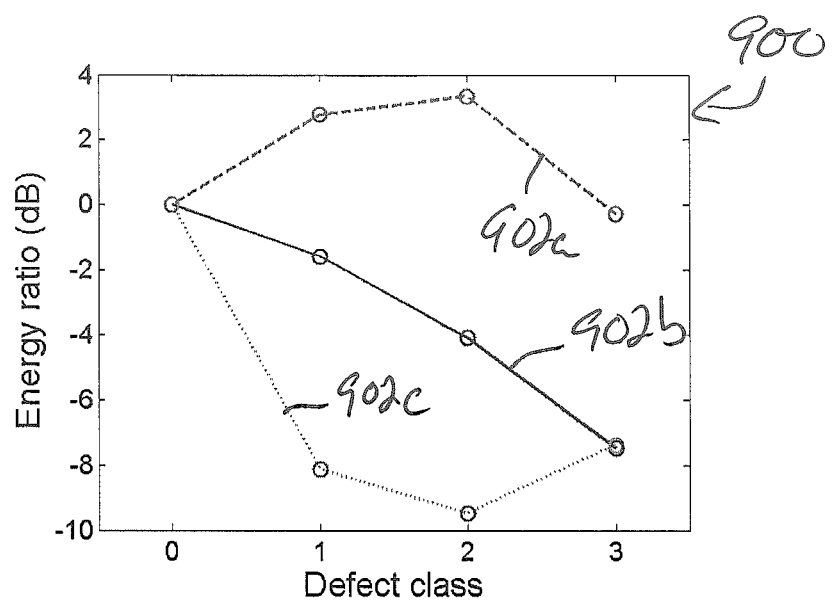
FIG. 10 is a graph that depicts an energy ratio versus defect class multiple mode activation points.

In some embodiments, the optimal mode activation region 802 does not correspond to the region with the greatest feature value. For example, in FIG. 9, a second region 804 has a greater feature value than the optimal mode activation region 802. The optimal mode activation region 802 is preferable to the second region 804, as the optimal mode activation region 802 has a steady, monotonic change in value as the defect damage condition increases. FIG. 10 is a graph 900 illustrating the energy ratio feature versus bond length (defect class) for three different mode activation points 902a-902c. The illustrated mode activation points 902a-902c comprise one "good" mode activation point 902b and two "poor" mode activation points 902a, 902c based on feature correlation with bond length. For example, in the experimental set-up illustrated in FIG. 5A, the good mode activation point 902b has a phase velocity of 2.85 mm/µs and a frequency of 0.485 MHz and the poor mode activation points 902a, 902c have respective phase velocities of 2.6 and 2.4 mm/µs and respective frequencies of 0.519 and 0.57 MHz.

As shown in FIG. 10, the energy ratio feature for the good mode activation point 902b shows a monotonically decreasing trend with increasing defect class. The monotonically decreasing trend correlates with bond length when performing an inspection of a surface. The two poor mode activation points 902a, 902c show non-monotonic trends. In some embodiments, mode activation points having both monotonic and non-monotonic trends may be combined to by the controller 530 to generate a pattern recognition search algorithm providing a robust defect detection scheme.

Figure 11:
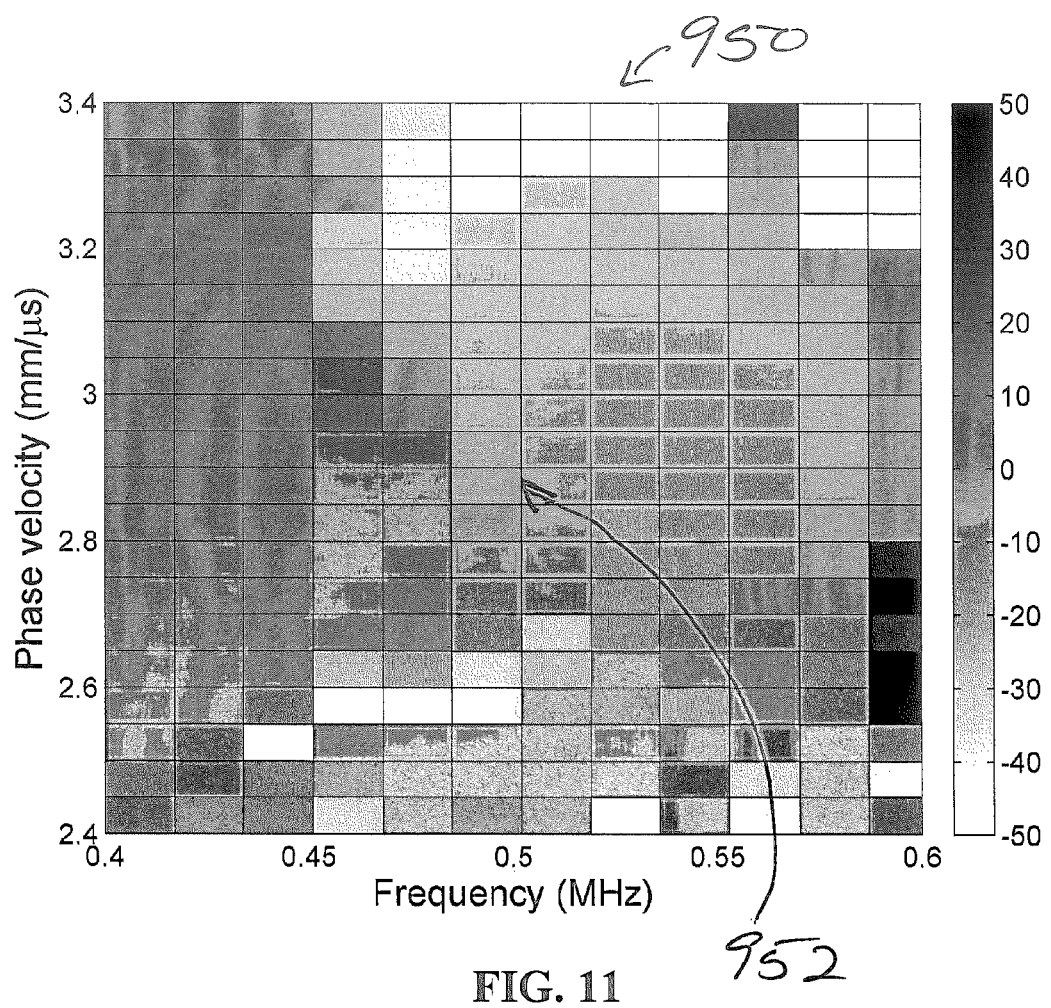
FIG. 11 is a plot of the mean of the frequency shift feature for multiple defect classes.

In some embodiments, the controller 530 may be configured to optimize a frequency shift feature. A frequency shift feature may be defined as a change in the frequency of maximum amplitude in Fast Fourier Transform (FFT). The frequency shift feature may be determined by finding the frequency of maximum amplitude in the FFT for a first waveform that has traveled through a bonded region and subtracting the maximum amplitude for the first waveform from the frequency of maximum amplitude in the FFT from the zero bond case. FIG. 11 illustrates the mean of the frequency shift feature for the three defect classes discussed with respect to FIGS. 8A-8C above.

As shown in FIG. 11, an optimized mode activation region 952 provides the largest change in the frequency shift feature. The optimal mode activation region 952 is located at about a phase velocity of 2.9 mm/µs and a frequency of about 0.45 MHz. The optimal mode activation region 952 has a higher sensitivity to the frequency shift feature than other excitation frequencies in the selected region 950. The optimal mode point 952 in the selected region 950 gives a 104% increase in feature value from the starting point. Similar to the energy ratio feature discussed above, the optimal mode activation region 952 for the frequency shift feature has a monotonic change.

Figure 12:
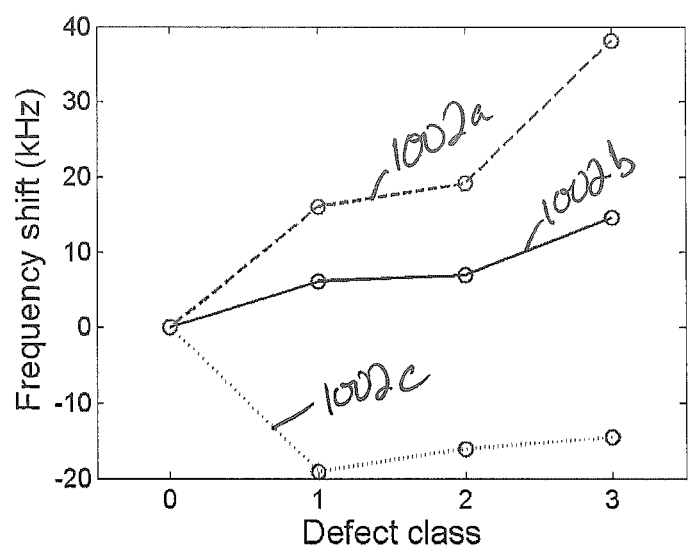
FIG. 12 is a graph depicting the frequency shift versus bond length for multiple mode activation points.

FIG. 12 illustrates the frequency shift feature versus defect class for three different mode activation points 1002a-1002c. The different mode activation points 1002a-1002c include two "good" activation points 1002a, 1002b and one "poor" activation point 1002c. For example, in the experimental set-up illustrated in FIG. 5A, the good activation points 1002a, 1002b comprise phase velocities of 2.9 mm/µs and frequencies of 0.4 and 0.468 MHz, respectively. The poor activation point 1002c comprises a phase velocity of 2.9 mm/µs and a frequency of 0.536 MHz. As shown in FIG. 12, the frequency shift feature value for good activation points 1002a, 1002b show a monotonically increasing trend with increasing defect classes. The second activation point 1002b (located at 0.468 MHz) shows a large change in the frequency shift than the first activation point 1002a (located at 0.4 MHz). The second activation point 1002b has a higher sensitivity to bond length defects and can detect smaller changes in bond length. Therefore, the second activation point 1002b is preferable for use in bond inspection when optimizing for defect sensitivity.

In various embodiments, the disclosed mode sweep techniques allow an inspection system, such as, for example, the inspection system 100, to be optimized for one or more nondestructive evaluations and inspections for structural health monitoring of structures. For example, in some embodiments, the inspection system 100 is optimized for: bond quality evaluation to identify no bond, kissing bond, weak bond, good bond, and/or identifying other types of bond conditions including the type, length, and/or location of a defect for 2 to n layer structures; identification of delaminations, kissing bonds, weak interfaces, voids, and/or other defects in composites; identification of surface corrosion detection, localization, and sizing on the surface of plates, curved surfaces, pipes, and/or multilayer structures, and between layers of multilayer structures; detection of cracks (small and/or large) including localization and sizing near the surface of plates, curved surfaces, pipes, and/or multilayer structures; identification of saw cuts, notches, and/or other surface defects where material has been removed from the surface of a structure; and/or identification of material hardening, radiation damage, dislocation, and/or other microstructure changes that have been shown to be indicators to macro-scale cracks and/or other damage before it appears.

Figure 13:
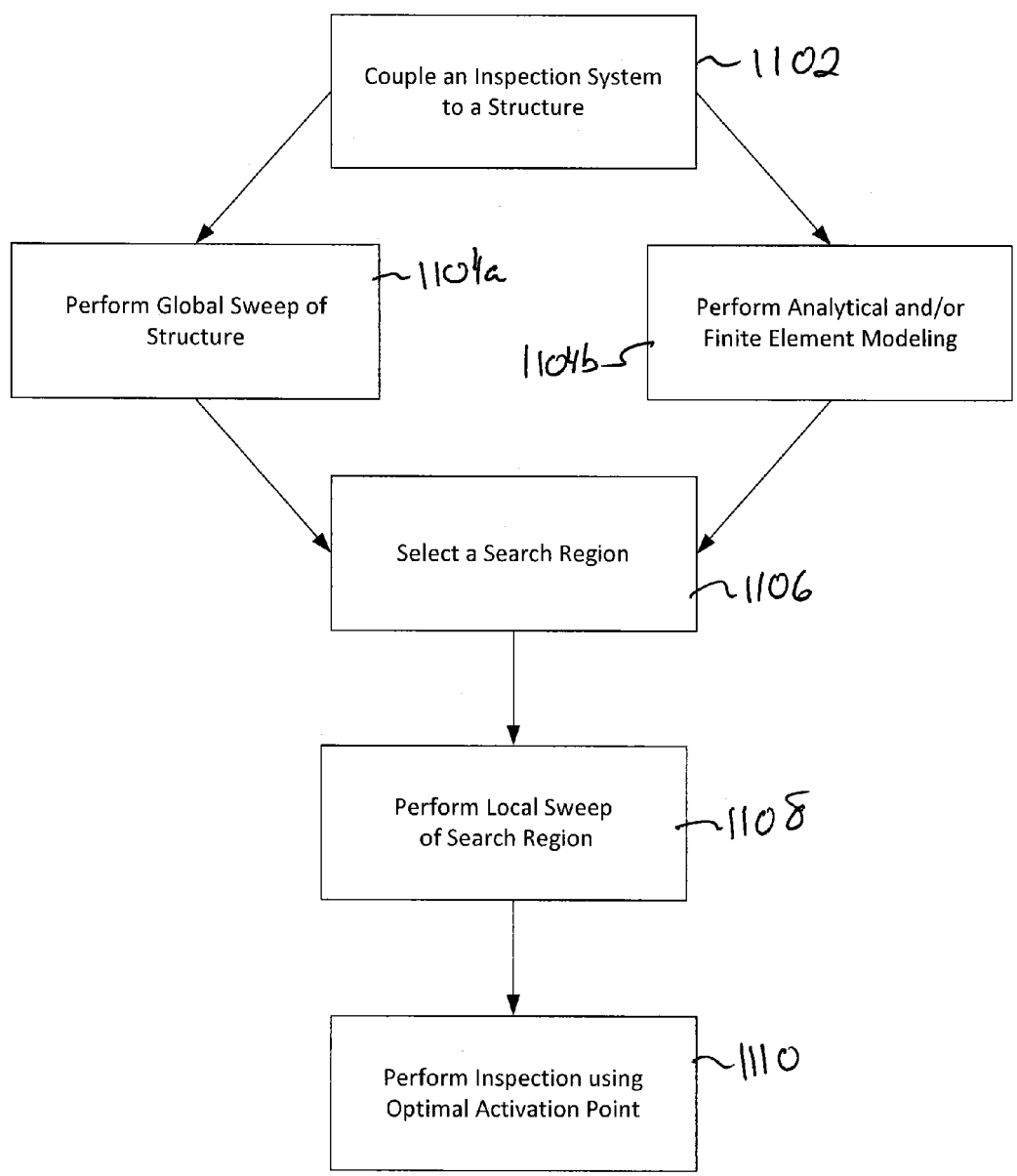
FIG. 13 is a flowchart illustrating one embodiment of a method of inspecting a structure.

FIG. 13 is a flowchart illustrating one embodiment of a method 1100 of inspecting a structure. In a first step 1102, an inspection system is coupled to a structure. The inspection system may comprise any suitable inspection system configured to generate guided waves in the structure. The inspection system comprises at least one transducer and a controller electrically coupled to the transducer. For example, the inspection system may comprise the inspection systems 100, 500, 550 illustrated in FIGS. 1A, 1B, 6A, and 6B. The inspection system generates guided waves in the structure and can be adjusted to activate a plurality of guided wave mode points.

In a second step 1104a, the transducer of the inspection system is used to perform a global sweep of the structure. In the global sweep, a plurality of mode activation points are activated in the structure. The plurality of mode activation points are located in a region of a dispersion curve of the structure encompassing a plurality of guided wave modes. The global sweep identifies regions of interest that have guided wave mode responses that optimize one or more inspection parameters. Alternatively, in a second step 1104b, potential search regions are identified by performing analytical and/or finite element modeling of the waveguide structure to identify promising search regions for a local scan. The analytical and/or finite element modeling identifies modes and frequencies that may be used to establish a search region for optimizing one or more parameters during a local scan.

In a third step 1106, a search region is selected from the identified regions of interest. The controller of the inspection system selects the search region. The controller may select a search region by, for example, identifying the region of interest with the optimal mode response for one or more search parameters. For example, the search region may be selected to optimize the guided wave penetration, transducer frequency, energy ratio of a guided wave, a frequency shift feature, and/or any other guided wave parameter or any combination thereof.

After selecting a search region in a third step 1106, a local scan is performed in a fourth step 1108. The local scan comprises activating a plurality of mode activation points within the search region to identify the mode activation point with an optimal response for the selected guided wave search parameters. The optimal activation point is identified by the controller. In a fifth step 1110, the optimal activation point is used to perform an inspection of the structure to identify defects in the structure, such as, for example, weld issues, cracks in the structure, and/or any other detectable structural issue. After inspecting the structure, additional mode activation points may be selected for optimizing additional and/or alternative guide wave mode parameters.

Although the subject matter has been described in terms of exemplary embodiments, it is not limited thereto. Rather, the appended claims should be construed broadly, to include other variants and embodiments, which may be made by those skilled in the art.

What is claimed is:

1. A method of inspecting a structure, the method comprising:
    selecting a search region of a dispersion curve of the structure corresponding to one or more inspection parameters, wherein the search region comprises at least one guided wave mode activation point not located on the dispersion curve;
    activating, using an inspection system comprising at least one transducer, a plurality of activation points located within the search region of the dispersion curve, wherein the search region comprises a fine tuning grid; and
    identifying an optimal activation point for the one or more inspection parameters, wherein the optimal activation point comprises at least one of the plurality of activation points producing an optimal response for the one or more inspection parameters.

2. The method of claim 1, wherein activating the plurality of activation points comprises generating a plurality of guided waves having variable phase velocities, frequencies, or both by activating at least one transducer, wherein the guided waves are generated in the structure.

3. The method of claim 2, wherein the variable phase velocities are generated by activating the at least one transducer with a time delay.

4. The method of claim 2, wherein the variable phase velocities are generated by adjusting an angle between the at least one transducer and the plate-like structure.

5. The method of claim 1, wherein the search region comprises a single mode of the dispersion curve.

6. The method of claim 1, wherein the search region comprises a mode crossing.

7. The method of claim 1, wherein prior to selecting a search region, the method comprises activating, using the inspection system, a plurality of activation points located within multiple regions of the dispersion curve to identify one or more potential search regions.

8. The method of claim 1, wherein the one or more inspection parameters comprise one of penetration power of a guided wave, energy ratio of a guided wave, a frequency shift feature, or any combination thereof.

9. The method of claim 8, wherein the optimal response comprises a monotonic change in at least one of the inspection parameters.

10. A system, comprising:
    at least one transducer configured to be coupled to a structure; and
    a controller electrically coupled to the at least one transducer, the controller comprising:
        a machine readable storage memory; and
        a processor in signal communication with the machine readable storage medium, the processor configured to:
            select a search region of a dispersion curve of the structure corresponding to one or more inspection parameters, wherein the search region comprises at least one guided wave mode activation point not located on the dispersion curve;
            activate a plurality of activation points located within the search region of the dispersion curve using the at least one transducer, wherein the search region comprises a fine tuning grid; and
            identify an optimal activation point for the one or more inspection parameters, wherein the optimal activation point comprises at least one of the plurality of activation points producing an optimal response for the one or more inspection parameters.

11. The system of claim 10, wherein activating the plurality of activation points comprises generating a plurality of guided waves having variable phase velocities, frequencies, or both by activating at least one transducer.

12. The system of claim 11, wherein the at least one transducer comprises a linear comb array transducer.

13. The system of claim 12, wherein the variable phase velocities are generated by activating the at least one transducer with a time delay.

14. The system of claim 11, wherein the at least one transducer comprises an angle beam probe.

15. The method of claim 14, wherein the variable phase velocities are generated by adjusting an angle between the at least one transducer and the structure.

16. The system of claim 10, wherein the search region comprises one of a single mode of the dispersion curve or a mode crossing.

17. The system of claim 10, wherein prior to selecting a search region, the processor is configured to active, using the at least one transducer, a plurality of activation points located within multiple regions of the dispersion curve to identify one or more potential search regions.

18. The method of claim 10, wherein the one or more inspection parameters comprise one of penetration power of a guided wave, energy ratio of a guided wave, a frequency shift feature, or any combination thereof.

19. A method, comprising:
    activating, using an inspection system, a plurality of activation points located in a structure to identify one or more potential search regions, wherein the plurality of activation points are selected from a dispersion curve of the structure, and wherein the inspection system comprises at least one transducer;
    selecting a search region from the potential search regions corresponding to one or more inspection parameters, wherein the search region comprises at least one guided wave mode activation point not located on the dispersion curve;
    activating, using the inspection system, a plurality of activation points located within the search region of the dispersion curve, wherein activating the plurality of activation points comprises generating a plurality of guided waves having variable phase velocities, frequencies, or both by activating at least one transducer, wherein the search region comprises a fine tuning grid; and identifying an optimal activation point for the one or more inspection parameters, wherein the optimal activation point comprises at least one of the plurality of activation points producing an optimal response for the one or more inspection parameters, and wherein the optimal response comprises an effective wave resonance.

* * * * *